United States Patent
Anderson et al.

(12)

(10) Patent No.: US 6,252,045 B1
(45) Date of Patent: Jun. 26, 2001

(54) HUMAN OCCLUDIN, ITS USES AND ENHANCEMENT OF DRUG ABSORPTION USING OCCLUDIN INHIBITORS

(75) Inventors: James M. Anderson; Christina M. Van Itallie, both of New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/142,732

(22) PCT Filed: Mar. 14, 1997

(86) PCT No.: PCT/US97/05809

§ 371 Date: Sep. 15, 1998

§ 102(e) Date: Sep. 15, 1998

(87) PCT Pub. No.: WO97/33605

PCT Pub. Date: Sep. 18, 1997

Related U.S. Application Data

(60) Provisional application No. 60/013,625, filed on Mar. 15, 1996.

(51) Int. Cl.[7] ....................................................... C07K 1/00
(52) U.S. Cl. ............................ 530/350; 530/324; 435/7.1
(58) Field of Search ................................... 530/350, 324; 435/7.1

(56) References Cited

PUBLICATIONS

Ngo et al. The Protein Folding Problem and Tertiary Structure Prediction pp. 433 & 492 & 495, 1994.*

* cited by examiner

*Primary Examiner*—Patrick J. Nolan
(74) *Attorney, Agent, or Firm*—Mary M. Krinsky

(57) ABSTRACT

The gene for occludin, an integral transmembrane protein specifically associated with tight junctions that functions in forming intercellular seal, is cloned, characterized, and sequenced, and the polypeptide sequence determined. Drug delivery is enhanced by administering an effective amount of occludin inhibitors. These include peptides or antibodies that interact with occludin or occludin receptors. Also included are occludin antagonists, occludin receptor components, and mixtures thereof. In some embodiments, analogues of occludin surface loops that inhibit adhesion and/or barrier properties are employed. Administration can be local or systemic; local administration in a pharmaceutically acceptable carrier is preferred in some embodiments.

18 Claims, 14 Drawing Sheets

Figure 1

```
      GCCTCTCTCCATCAGACACCCCAAGGTTCC
1     ------------------------------ 30
      CGGAGAGAGGTAGTCTGTGGGGTTCCAAGG

ATCCGAAGCAGGCGGAGCACCGAACGCACC
31    ------------------------------ 60
      TAGGCTTCGTCCGCCTCGTGGCTTGCGTGG

CCGGGGTGGTCAGGGACCCCATCCGTGCT
61    ------------------------------ 90
      GGCCCCACCAGTCCCTGGGGGTAGGCACGA

GCCCCTAGGAGCCCGCGCCTCTCCTCTGC
91    ------------------------------ 120
      CGGGGGATCCTCGGGCGCGGAGAGGAGACG

GCCCGCCTCTCGGGCCGCAACATCGCGCG
121   ------------------------------ 150
      CGGGGCGGAGAGCCCGGCGTTGTAGCGCGC

GTTCCTTTAACAGCGCGCTGGCAGGGTGTG
151   ------------------------------ 180
      CAAGGAAATTGTCGCGCGACCGTCCCACAC

GGAAGCAGGACCGCGTCCTCCCGCCCCTC
181   ------------------------------ 210
      CCTTCGTCCTGGCGCAGGAGGGCGGGGGAG

CCATCCGAGTTTCAGGTGAATTGGTCACCG
211   ------------------------------ 240
      GGTAGGCTGAAAGTCCACTTAACCAGTGGC
```

```
      AGGGAGGAGGCCGACACACCACACCTACAC
241   ------------------------------   271
      TCCCTCCTCCGGCTGTGTGGTGTGGATGTG

TCCCGCGTCCACCTCTCCCTCCCTGCTTCC
271   ------------------------------   300
      AGGGCGCAGGTGGAGAGGGAGGGACGAAGG

TCTTGGCGGAGGCGGCAGGAACCGAGAGCC
301   ------------------------------   330
      AGAACCGCCTCCGCCGTCCTTGGCTCTCGG

AGGTCCAGAGCGCCGAGGAGCCGGTCTAGG
331   ------------------------------   360
      TCCAGGTCTCGCGGCTCCTCGGCCAGATCC

ACGCAGCAGATTGGTTTATCTTGGAAGCTA
361   ------------------------------   390
      TGCGTCGTCTAACCAAATAGAACCTTCGAT

AAGGGCATTGCTCATCCTGAAGATCAGCTG
391   ------------------------------   420
      TTCCCGTAACGAGTAGGACTTCTAGTCGAC
                           START
      ACCATTGACAATCAGCC ATG TCATCCAGGC
421   ------------------------------   450
      TGGTAACTGTTAGTCGGTACAGTAGGTCCG
                        M   S   S   R   P

CTCTTGAAAGTCCACCTCCTTACAGGCCTG
451   ------------------------------   480
      GAGAACTTTCAGGTGGAGGAATGTCCGGAC
       L   E   S   P   P   P   Y   R   P   D
```

```
        ATGAATTCAAACCGAATCATTATGCACCAA
481     ------------------------------ 510
        TACTTAAGTTTGGCTTAGTAATACGTGGTT
         E   F   K   P   N   H   Y   A   P   S

GCAATGACATATATGGTGGAGAGATGCATG
511     ------------------------------ 540
        CGTTACTGTATATACCACCTCTCTACGTAC
         N   D   I   Y   G   G   E   M   H   V

TTCGACCAATGCTCTCTCAGCCAGCCTACT
541     ------------------------------ 570
        AAGCTGGTTACGAGAGAGTCGGTCGGATGA
         R   P   M   L   S   Q   P   A   Y   S

CTTTTTACCCAGAAGATGAAATTCTTCACT
571     ------------------------------ 600
        GAAAAATGGGTGTTCTACTTTAAGAAGTGA
         F   Y   P   E   D   E   I   L   H   F

TCTACAAATGGACCTCTCCTCCAGGAGTGA
601     ------------------------------ 630
        AGATGTTTACCTGGAGAGGAGGTCCTCACT
         Y   K   W   T   S   P   P   G   V   I

TTCGGATCCTGTCTATGCTCATTATTGTGA
631     ------------------------------ 660
        AAGCCTAGGACAGATACGAGTAATAACACT
         R   I   L   S   M   L   I   I   V   M

TGTGCATTGCCATCTTTGCCTGTGTGGCCT
661     ------------------------------ 690
        ACACGTAACGGTAGAAACGGACACACCGGA
         C   I   A   I   F   A   C   V   A   S
```

```
            CCACGCTTGCCTGGGACAGAGGCTATGGAA
691         ------------------------------   720
            GGTGCGAACGGACCCTGTCTCCGATACCTT
             T  L  A  W  D  R  G  Y  G  T

CTTCCCTTTTAGGAGGTAGTGTAGGCTACC
721         ------------------------------   750
            GAAGGGAAAATCCTCCATCACATCCGATGG
             S  L  L  G  G  S  V  G  Y  P

CTTATGGAGGAAGTGGCTTTGGTAGCTACG
751         ------------------------------   780
            GAATACCTCCTTCACCGAAACCATCGATGC
             Y  G  G  S  G  F  G  S  Y  G

GAAGTGGCTATGGCTATGGCTATGGTTATG
781         ------------------------------   810
            CTTCACCGATACCGATACCGATACCAATAC
             S  G  Y  G  Y  G  Y  G  Y  G

GCTATGGCTACGGAGGCTATACAGACCCAA
811         ------------------------------   840
            CGATACCGATGCCTCCGATATGTCTGGGTT
             Y  G  Y  G  G  Y  T  D  P  R

GAGCAGCAAAGGGCTTCATGTTGGCCATGG
841         ------------------------------   870
            CTCGTCGTTTCCCGAAGTACAACCGGTACC
             A  A  K  G  F  M  L  A  M  A

CTGCCTTTTGTTTCATTGCCGCGTTGGTGA
871         ------------------------------   900
            GACGGAAAACAAAGTAACGGCGCAACCACT
             A  F  C  F  I  A  A  L  V  I
```

```
        TCTTTGTTACCAGTGTTATAAGATCTGAAA
901     ------------------------------ 930
        AGAAACAATGGTCACAATATTCTAGACTTT
         F   V   T   S   V   I   R   S   E   M

TGTCCAGAACAAGAAGATACTACTTAAGTG
931     ------------------------------ 960
        ACAGGTCTTGTTCTTCTATGATGAATTCAC
         S   R   T   R   R   Y   Y   L   S   V

TGATAATAGTGAGTGCTATCCTGGGCATCA
961     ------------------------------ 990
        ACTATTATCACTCACGATAGGACCCGTAGT
         I   I   V   S   A   I   L   G   I   M

TGGTGTTTATTGCCACAATTGTCTATATAA
991     ------------------------------ 1020
        ACCACAAATAACGGTCTTAACAGATATATT
         V   F   I   A   T   I   V   Y   I   M

TGGGAGTGAACCCAACTGCTCAGTCTTCTG
1021    ------------------------------ 1050
        ACCCTCACTTGGGTTGACGAGTCAGAAGAC
        | G   V   N   P   T   A   Q   S   S   G |

GATCTCTATATGGTTCACAAATATATGCCC
1051    ------------------------------ 1080
        CTAGAGATATACCAAGTCTTTATATACGGG
        | S   L   Y   G   S   Q   I   Y   A   L |

TCTGCAACCAATTTTATACACCTGCAGCTA
1081    ------------------------------ 1110
        AGACGTTGGTTAAAATATGTGGACGTCGAT
        | C   N   Q   F   Y   T   P   A   A   T |
```

```
       CTGGACTCTACGTGGATCAGTATTTGTATC
1111   ------------------------------ 1140
       GACCTGAGATCGACCTAGTCATAAACATAG
        G  L  Y  V  D  Q  Y  L  Y  H

ACTACTGTGTTGTGGATCCCCAGGAGGCCA
1141   ------------------------------ 1170
       TGATGACACAACACCTAGGGGTCCTCCGGT
        Y  C  V  V  D  P  Q  E  A  I

TTGCCATTGTACTGGGGTTCATGATTATTG
1171   ------------------------------ 1200
       AACGGTAACATGACCCCAAGTACTAATAAC
        A  I  V  L  G  F  M  I  I  V

TGGCTTTTGCTTTAATAATTTTCTTTGCTG
1201   ------------------------------ 1230
       ACCGAAAACGAAATTATTAAAGAAACGAC
        A  F  A  L  I  I  F  F  A  V

TGAAAACTCGAAGAAGATGGACAGGTATG
1231   ------------------------------ 1260
       ACTTTTGAGCTTCTTTCTACCTGTCCATAC
         K  T  R  R  K  M  D  R  Y  D

ACAAGTCCAATATTTGTGGGACAAGGAAC
1261   ------------------------------ 1290
       TGTTCAGGTTATAAACACCCTGTTCCTTG
           K  S  N  I  L  W  D  K  E  H

ACATTTATGATGAGCAGCCCCCAATGTCG
1291   ------------------------------ 1320
       TGTAAATACTACTCGTCGGGGGGTTACAGC
          I  Y  D  E  Q  P  P  N  V  E
```

```
          AGGAGTGGGTTAAAAATGTGTCTGCAGGCA
1321      ------------------------------      1350
          TCCTCACCCAATTTTTACACAGACGTCCGT
           E   W   V   K   N   V   S   A   G   T

CACAGGACGTGCCTTCACCCCCATCTGACT
1351      ------------------------------      1380
          GTGTCCTGCACGGAAGTGGGGGATGACTGA
           Q   D   V   P   S   P   P   S   D   Y

ATGTGGAAAGAGTTGACAGTCCCATGGCAT
1381      ------------------------------      1410
          ATCACCTTTCTCAACTGTCAGGGTACCGTA
           V   E   R   V   D   S   P   M   A   Y

ACTCTTCCAATGGCAAAGTGAATGACAAGC
1411      ------------------------------      1440
          TGAGAAGGTTACCGTTTCACTTACTGTTCG
           S   S   N   G   K   V   N   D   K   R

GGTTTTATCCAGAGTCTTCCTATAAATCCA
1441      ------------------------------      1470
          CCAAAATAGGTCTCAGAAGGATATTTAGGT
           F   Y   P   E   S   S   Y   K   S   T

CGCCGGTTCCTGAAGTGGTTCAGGAGCTTC
1471      ------------------------------      1500
          GCGGCCAAGGACTTCACCAAGTGGTCGAAG
           P   V   P   E   V   V   Q   E   L   P

CATTAACTTCGCCTGTGGATGACTTCAGGC
1501      ------------------------------      1530
          GTAATTGAAGCGGACACCTACTCAAGTCCG
           L   T   S   P   V   D   D   F   R   Q
```

```
           AGCCTCGTTACAGCAGCGGTGGTAACTTTG
1531       ------------------------------ 1560
           TCGGAGCAATGTCGTCGCCACCATTGAAAC
            P  R  Y  S  S  G  G  N  F  E

AGACACCTTCAAAAAGAGCACCTGCAAAGG
1561       ------------------------------ 1590
           TCTGTGGAAGTTTTTCTCGTGGACGTTTCC
            T  P  S  K  R  A  P  A  K  G

GAAGAGCAGGAAGGTCAAAGAGAACAGAGC
1591       ------------------------------ 1620
           CTTCTCGTCCTTCCAGTTTCTCTTGTCTCG
            R  A  G  R  S  K  R  T  E  Q

AAGATCACTATGAGACAGACTACACAACTG
1621       ------------------------------ 1650
           TTCTAGTGATACTCTGTCTGATGTGTTGAC
            D  H  Y  E  T  D  Y  T  T  G

GCGGCGAGTCCTGTGATGAGCTGGAGGAGG
1651       ------------------------------ 1680
           CGCCGCTCAGGACACTACTCGACCTCCTCC
            G  E  S  C  D  E  L  E  E  D

ACTGGATCAGGGAATATCCACCTATCACTT
1681       ------------------------------ 1710
           TGACCTAGTCCCTTATAGGTGGATAGTGAA
            W  I  R  E  Y  P  P  I  T  S

CAGATCAACAAAGACAACTGTACAAGAGGA
1711       ------------------------------ 1740
           GTCTAGTTGTTTCTGTTGACATGTTCTCCT
            D  Q  Q  R  Q  L  Y  K  R  N
```

```
          ATTTTGACACTGGCCTACAGGAATACAAGA
     1741 ------------------------------ 1770
          TAAAACTGTGACCGGATGTCCTTATGTTCT
            F   D   T   G   L   Q   E   Y   K   S

GCTTACAATCAGAACTTGATGAGATCAATA
     1771 ------------------------------ 1800
          CGAATGTTAGTCTTGAACTACTCTAGTTAT
            L   Q   S   E   L   D   E   I   N   K

AAGAACTCTCCCGTTTGGATAAAGAATTGG
     1801 ------------------------------ 1830
          TTCTTGAGAGGGCAAACCTATTTCTTAACC
            E   L   S   R   L   D   K   E   L   D

ATGACTATAGAGAAGAAAGTGAAGAGTACA
     1831 ------------------------------ 1860
          TACTGATATCTCTTCTTTCACTTCTCATGT
            D   Y   R   E   E   S   E   E   Y   M

TGGCTGCTGCTGATGAATACAATAGACTGA
     1861 ------------------------------ 1890
          ACCGACGACGACTACTTATGTTATCTGACT
            A   A   A   D   E   Y   N   R   L   K

AGCAAGTGAAGGGATCTGCAGATTACAAAA
     1891 ------------------------------ 1920
          TCGTTCACTTCCCTAGACGTCTAATGTTTT
            Q   V   K   G   S   A   D   Y   K   S

GTAAGAAGAATCATTGCAAGCAGTTAAAGA
     1921 ------------------------------ 1950
          CATTCTTCTTAGTAACGTTCGTCAATTTCT
            K   K   N   H   C   K   Q   L   K   S
```

```
            GCAAATTGTCACACATCAAGAAGATGGTTG
1951        ------------------------------        1980
            CGTTTAACAGTGTGTAGTTCTTCTACCAAC
             K   L   S   H   I   K   K   M   V   G
                                             STOP
            GAGACTATGATAGACAGAAACA|TAG|AAGG
1981        ------------------------------        2010
            CTCTGATACTATCTGTCTTTTGTATCTTCC
             D   Y   D   R   Q   K   T

CTGATGCCAAGTTGTTTGAGAAATTAAGTA
2011        ------------------------------        2040
            GACTACGGTTCAACAAACTCTTTAATTCAT

TCTGACATCTCTGCAATCTTCTCAGAAGGC
2041        ------------------------------        2070
            AGACTGTAGAGACGTTAGAAGAGTCTTCCG

AAATGACTTTGGACCATAACCCCGGAAGCC
2071        ------------------------------        2100
            TTTACTGAAACCTGGTATTGGGGCCTTCGG

AAACCTCTGTGAGCATCACAAAGTTTTGGG
2101        ------------------------------        2130
            TTTGGAGACACTCGTAGTGTTTCAAAACCC

TTGCTTTAACATCATCAGTATTGAAGCATT
2131        ------------------------------        2160
            AACGAAATTGTAGTAGTCATAACTTCGTAA

TTATAAATCGCTTTTGATAATCAACTGGGC
2161        ------------------------------        2190
            AATATTTAGCGAAAACTATTAGTTGACCCG
```

```
         TGAACAACTCCAATTAAGGATTTTATGCTT
2191     ------------------------------ 2220
         ACTTGTTGAGGTTAATTCCTAAAATACGAA

TAAACATTGGTTCTTGTATTAAGAATGAAA
2221     ------------------------------ 2250
         ATTTGTAACCAAGAACATAATTCTTACTTT

TACTGTTTGAGGTTTTTAAGCCTTAAAGGA
2251     ------------------------------ 2280
         ATGACAAACTCCAAAAATTCGGAATTTCCT

AGGTTCTGGTGTGAACTAAACTTTCACACC
2281     ------------------------------ 2310
         TCCAAGACCACACTTGATTTGAAAGTGTGG

CC
2311     -- 2312
         GG
```

HUMAN OCCLUDIN, ITS USES AND ENHANCEMENT OF DRUG ABSORPTION USING OCCLUDIN INHIBITORS

RELATED APPLICATION DATA

This is a continuation-in-part of U.S. patent application Ser. No. 60/013,625, filed Mar. 15, 1996 which is a 371 of PCT/US97/05809 filed Mar. 14, 1997.

The invention was made with partial government support with NIH R01 DK45134, NIH P01 DK38979, and NCI CA66263 grants. The government has certain rights in the invention.

TECHNICAL FIELD

This invention relates primarily to the enhancement of drug absorption across epithelial and endothelial barriers using occludin inhibitors.

BACKGROUND OF THE INVENTION

In mammalian cells, intercellular junctions are typically categorized into four types, based on early electron microscope studies: adherens junctions, desmosomes, gap junctions, and tight junctions. Recent research interest has focused on the molecular organization and functions of these junctions, to not only explain cell-cell interactions and communication within multi-cellular organisms, but also to regulate paracellular permeability for therapeutic purposes.

Drug absorption across epithelial and endothelial tissue is limited in several stages. One important barrier is created by intercellular tight junctions which limit movement of substances between cells (Anderson, J. M., and Van Itallie, C. M., *Am. J. Physiol.* (GI and Liver) 269:G467–G475 (1995)). The tight junction barrier appears to be created by extracellular contacts of a transmembrane protein called occludin. The protein was originally cloned from the chicken (Furuse, M., et al., *J. Cell Biol.* 123: 1777–1788 (1993)). Occludin has subsequently been cloned and sequenced from human, mouse, dog and rat kangaroo (Ando-Akatsuka, Y., et al., *J Cell Biology* 133: 43–47 (1996). Human occludin has also been cloned and sequenced by applicants (Genbank Accession U53823; see SEQ ID NOs 1 and 2 and FIG. 1).

Tight junctions create a regulated paracellular barrier to the movement of water, solutes, macromolecules, immune cells, and the like between and among both epithelial and endothelial cells. New evidence has elucidated information about proteins involved in this dynamic regulation.

It would be beneficial to utilize this information to alter paracellular permeability for specific medical purposes.

SUMMARY OF THE INVENTION

It is an object of the invention to provide the sequence of cloned human occludin.

It is another object of the invention to provide a method for the selective enhancement of transmucosal or transvascular drug delivery. It has been demonstrated that peptides corresponding to the extracellular fragments of human occludin are capable of inhibiting cell to cell adhesion (see the examples that follow). Further it has been shown that peptides corresponding to extracellular sequences of occludin can interrupt the transmonolayer barrier properties of cultured epithelial cells (Wong and Gumbiner, B. (1997) *J. Cell Biology* 136:399–409. Also see FIG. 2.

These and other objects are accomplished by the present invention, which provides cloned human occludin and methods for altering occludin's barrier properties. The sequence of occludin provides occludin-based screening assays for occludin inhibitors such as binding assays, assays that measure adhesive properties, and the like, particularly those involving the extracellular loop sequences given below. In some embodiments, fibroblast adhesion measurements, e.g., those employing electrical resistance or transmonolayer flux measurements are employed.

In other embodiments, the invention provides a method for enhancing drug delivery by disrupting the intercellular seal provided by occludin. In accordance with this embodiment of the invention, effective amounts of occludin inhibitors and/or mimics such as peptide fragments of occludin and the like compounds identified in screens are administered to a patient, typically in combination with another drug or a mixture of drugs. Mimics include, but are not limited to, peptides analogous to sequences disclosed herein that have sequence alterations that enhance solubility or other properties desirable for achieving desirable pharmacological effects described hereafter. Administration can be local or systemic; local administration is preferred in some embodiments.

BRIEF DESCRIPTION OF THE FIGURES

FIG. 1 sets out the cDNA sequence of human occludin (SEQ ID NO 1) and the deduced amino acid sequence (SEQ ID NO 2). The figure employs standard one-letter nomenclature for the amino acids: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr. The extracellular loops described hereafter are denoted as boxed regions, as are the positions wherein translation starts and stops.

DETAILED DESCRIPTION OF THE INVENTION

Figure 2:
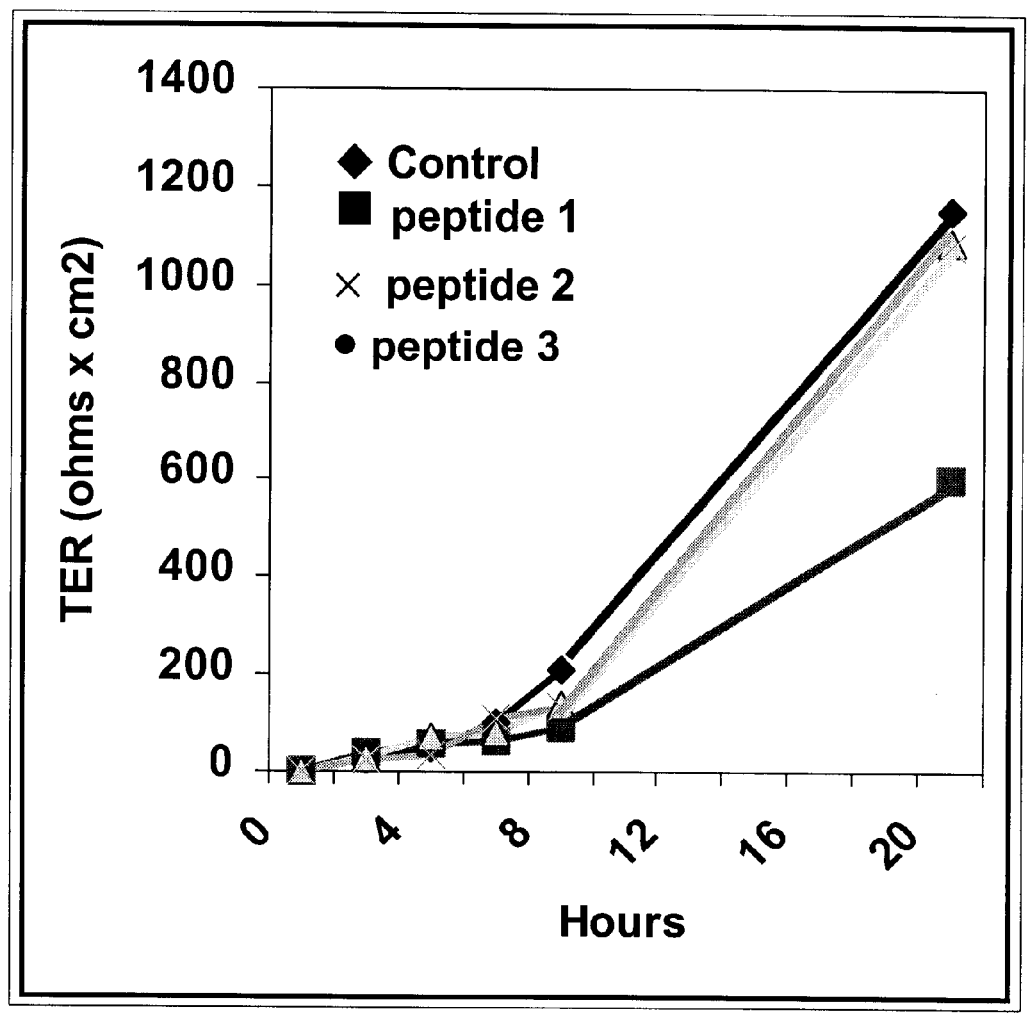
FIG. 2 is a graph showing inhibition of occludin-dependent intercellular adhesion using extracellular loop peptides corresponding to the N-terminal half of occludin extracellular loop #1 (peptide 1, SEQ ID NO 3) and the C-terminal half of extracellular loop #1 (peptide 2, SEQ ID NO 4) compared with an irrelevant peptide (peptide 3, SEQ ID NO 6). Caco-2 cells were plated on Falcon transwell cell culture inserts in DMEM supplemented with 10% fetal bovine serum and allowed to attach for 24 hours. Confluent monolayers were washed three times with calcium- and magnesium-free phosphate buffered saline and incubated in low calcium medium (supplemented with 5% dialyzed fetal bovine serum) for 24 hours. Transepithelial electrical ressitance was measured (time 0) and an equal volume of 2×DMEM/20% fetal bovine serum was added to all wells. To some wells, peptides were added with the fresh media. All peptides were added to a final concentration of 100 $\mu$M; transepithelial electrical resistance was measured in 3 wells of each treatment condition. Symbols represent the mean and standard deviation of each measurement.

This invention is based upon the elucidation of the sequence of human occludin. DNA sequences encoding human occludin were cloned, characterized, and sequenced, and the amino acid sequence of the polypeptide was deduced. See FIG. 1. The data show that the two extracellular domains of human occludin contain a highly unique amino acid sequence rich in tyrosine and glycine residues. The more amino-terminal extracellular domain of human occludin contains nine repeats of the dipeptide glycine/tyrosine. Comparison of the 5 available deduced amino acid sequences of occludin from different species demonstrates that the first loop in all species is very tyrosine- and glycine-rich. However, the amino acid sequence itself is not well conserved suggesting something unique about the chemical properties but not necessarily the specific amino acid sequence. In contrast, comparison of the second extracellular loop demonstrates a very conserved sequence. Both extracellular loops then provide a unique opportunity to develop inhibitors. In the case of loop 1, this would be more dependent on its unusual chemistry or be species-specific. Drugs developed for human use may not be active in other animal species. In the case of the second loop, there is a specific sequence requirement conserved across species.

This invention thus provides isolated and purified human occludin, and fragments thereof useful for therepeutic purposes, and purified and isolated DNA comprising DNA sequences encoding human occludin (and fragments thereof), and purified and isolated DNA comprising DNA sequences which hybridize under stringent conditions with sequences encoding the protein or its fragments. Also provided are RNA sequences corresponding to the DNA sequences.

In one embodiment, the invention provides purified and isolated DNA encoding the deduced human occludin set out in FIG. 1 (residues 534 to 2003 of SEQ ID NO: 1), degenerate and complimentary sequences, and sequences that hybridize under stringent conditions with the sequence. Also encompassed by this invention are cloned sequences defining human occludin, which can then be used to transform or transfect a host cell for protein expression using standard means. Also encompassed by this invention are DNA sequences homologous or closely related to complementary DNA described herein, namely DNA sequences which hybridize to occludin cDNA, particularly under stringent conditions that result in pairing only between nucleic acid fragments that have a high frequency of complementary base sequences, and RNA corresponding thereto. In addition to the occludin-encoding sequences, DNA encompassed by this invention may contain additional sequences, depending upon vector construction sequences, that facilitate expression of the gene. Also encompassed are sequences encoding synthetic occludin peptides or polypeptides exhibiting activity and structure similar to isolated or cloned occludin, particularly those that are active in inhibiting epithelial and endothelial barriers. These are referred to herein as "biological equivalents or variants," and in some embodiments have at least about 80%, preferably at least about 90% sequence homology with occludin.

Because of the degeneracy of the genetic code, a variety of codon change combinations can be selected to form DNA that encodes occludin of this invention, so that any nucleotide deletion(s), addition(s), or point mutation(s) that result in a DNA encoding the protein are encompassed by this invention. Since certain codons are more efficient for polypeptide expression in certain types of organisms, the selection of gene alterations to yield DNA material that codes for the protein of this invention are preferably those that yield the most efficient expression in the type of organism which is to serve as the host of the recombinant vector. Altered codon selection may also depend upon vector construction considerations.

DNA starting material which is employed to form DNA coding for occludin peptides or polypeptides of this invention may be natural, recombinant or synthetic. Thus, DNA starting material isolated from tissue or tissue culture, constructed from oligonucleotides using conventional methods, obtained commercially, or prepared by isolating RNA coding for occludin, and using this RNA to synthesize single-stranded cDNA which is used as a template to synthesize the corresponding double stranded DNA, can be employed to prepare DNA of this invention.

DNA encoding the peptides or polypeptides of this invention, or RNA corresponding thereto, are then inserted into a vector, and the recombinant vector used to transform a microbial host organism. Example host organisms useful in the invention include, but are not limited to, bacterial (e.g., E. coli or B. subtilis), yeast (e.g., S. cerevisiae), mammalian (e.g., mouse fibroblast or other cell line) or insect (e.g., baculovirus expression system) cells. This invention thus also provides novel, biologically functional viral and circular plasmid RNA and DNA vectors incorporating RNA and DNA sequences describing occludin or occludin fragments generated by standard means. Culture of host organisms stably transformed or transfected with such vectors under conditions facilitative of large scale expression of the exogenous, vector-borne DNA or RNA sequences and isolation of the desired polypeptides from the growth medium, cellular lysates, or cellular membrane fractions yields the desired products.

The present invention thus provides for the total and/or partial manufacture of DNA sequences coding for occludin, and including such advantageous characteristics as incorporation of codons preferred for expression by selected non-mammalian hosts, provision of sites of cleavage by restriction endonuclease enzymes, and provision of additional initial, terminal or intermediate DNA sequences which facilitate construction of readily expressed vectors. Correspondingly, the present invention provides for manufacture (and development by site specific mutagenesis of cDNA and genomic DNA) of DNA sequences coding for microbial expression of occludin analogues which differ from the form specifically described herein in terms of identity or location of one or more amino acid residues (i.e., deletion analogues containing less than all of the residues specified for the protein, and/or substitution analogues wherein one or more residues are added to a terminal or a medial portion of the polypeptide), and which share or alter the biological properties of occludin described herein.

DNA (and RNA) sequences of this invention code for all sequences useful in securing expression in procaryotic or eucaryotic host cells of peptide or polypeptide products having at least a part of the primary structural conformation, and one or more of the biological properties of occludin which are comprehended by: (a) the DNA sequences encoding occludin as described herein, or complementary strands; (b) DNA sequences which hybridize (under hybridization conditions) to DNA sequences defined in (a) or fragments thereof; and (c) DNA sequences which, but for the degeneracy of the genetic code, would hybridize to the DNA sequences defined in (a) and (b) above. Specifically comprehended are genomic DNA sequences encoding allelic variant forms of occludin included therein, and sequences encoding RNA, fragments thereof, and analogues wherein RNA or DNA sequences may incorporate codons facilitating transcription or RNA replication of messenger RNA in non-vertebrate hosts.

The results in the examples that follow show that the human cDNA can be transfected into cultured fibroblasts. Fibroblasts do not express occludin; they live as single cells and do not form barriers. Introduction of occludin into fibroblasts causes them to adhere to one another. Two separate peptides corresponding to the first and second half of the first extracellular loop have been shown to inhibit the cell/cell adhesion in occludin-transfected fibroblasts in a quantitative assay that measures cell-to-cell adhesion. This shows that the first loop is involved in an adhesive event and that the peptides themselves are competitive inhibitors of adhesion. FIG. 2 provides data showing this same peptide inhibits transmonolayer electrical resistance in cultured human colonic epithelial cells. Thus, the peptides are occludin inhibitors. Data reported in Wong and Gumbiner (cited above) demonstrate that the second loop is able to interfere with barrier properties of cultured monolayers and increase flux of tracer molecules.

The invention thus also provides the occludin peptides or polypeptides encoded by the above-described DNA and/or RNA, obtained by isolation or recombinant means. In one embodiment, for example, the invention provides a polypeptide having an amino acid sequence depicted in residues numbered 58 to 104 of human occludin depicted in FIG. 1 (residues 90 to 138 of SEQ ID NO 2), or fragments or biological variants thereof. In another embodiment, the invention provides a polypeptide having the amino acid sequence depicted in residues numbered 164 to 211 of the human occludin depicted in FIG. 1 (residues 196 to 246 of SEQ ID NO 2), or fragments or biological variants thereof.

The invention correspondingly provides peptide mimics such as peptide fragments of occludin and functionally equivalent counterparts that demonstrate activity in barrier disruption. For example, alterations in known sequences can be performed to enhance solubility or other properties desirable for the pharmacologic effect. Since the extracellular loops are involved as receptors in adhesion and sealing, the sequences can be used in in vivo assays to screen for receptor ligand agents which interrupt their adhesive properties.

For the construction of shorter peptides, preferred syntheses of occludin fragments of the invention may be by standard chemical means involving the ordered assembly of the peptides from constitutent amino acids. It is an advantage of the invention that since the two extracellular domains of human occludin exhibit a highly unique amino acid chemistry, rich in glycine and tyrosine, many peptides of the invention may be easily manufactured using the two constituent amino acids. Moreover, the uniqueness of the region provides a novel target for compounds which selectively disrupt occludin's seal and enhance intercellular drug delivery.

Isolation and purification of peptides and polypeptides provided by the invention are by conventional means including, for example, preparative chromatographic separations such as affinity, ion-exchange, exclusion, partition, liquid and/or gas-liquid chromatography; zone, paper, thin layer, cellulose acetate membrane, agar gel, starch gel, and/or acrylamide gel electrophoresis; immunological separations, including those using monoclonal and/or polyclonal antibody preparations; and combinations of these with each other and with other separation techniques such as centrifugation and dialysis, and the like.

It is an advantage of the invention that the isolation and purification of human occludin provides a polypeptide that is useful in the development of compounds that selectively alter the intercellular seal for the purpose of enhancing transmucosal and transendothelial drug delivery. The delivery of larger materials, e.g., viral particles used for therapeutic gene delivery, can also be enhanced.

Peptide regions which interact with the sealing surface and disrupt the barrier properties define protein regions responsible for sealing. Synthetic compounds mimicking this chemistry can then tested for similar properties. In this approach, occludin is considered a cell surface receptor whose adhesion creates the barrier. If the seal is formed by homotypic contacts, then occudin is both the receptor and its ligand. The extracellular domains, or representative peptides, are used to establish in vitro binding assays, and these assays are used to screen for compounds that disrupt binding. Recombinant fragments could be used, for example, in routine ELISA binding assays, phage display libraries, bacterial libraries or other known methods that screen large combinations of peptide sequences or other compounds.

This invention thus provides a method for screening for occludin inhibitors. As used herein, an occludin inhibitor is any substance that enhances paracellular permeability through specific interaction with extracellular protein sequences of occludin. Occludin inhibitors are identified in screening assays when test compounds inhibit a functional property of occludin. In vitro assays, for example, test compounds that bind to the extracellular loops of occludin expressed as recombinant or synthetic peptides, fragments or derivatives thereof, particularly assays that bind to residues 90 to 138 of SEQ ID NO 2 and/or residues 196 to 246 of SEQ ID NO 2 (or fragments or variants, and mixtures of these). Any standard binding assay can be used to screen the interaction of large collections of test compounds with a target. Compounds that bind to occludin are potential occludin inhibitors.

Alternatively, in vitro assays based on the interruption of adhesive properties of the extracellular protein sequences of occludin expressed as recombinant, synthetic or altered sequences, or fragments thereof, for binding other sequences of occludin or occludin receptors are employed. For example, a fluorescent labelled fragment of occludin is released into the fluid phase and detected spectrophotometrically. Other assays include fibroblast adhesion assays such as those described in the examples that follow, or binding of occludin-transfected fibroblasts to a solid phase on which test compounds are bound. Some assays involve transmonolayer flux measurements. Any test compound which inhibits occludin binding is identified as an occludin inhibitor for further evaluation.

In one embodiment of the invention, the method screens for the presence or absence of occludin inhibition by a test sample by (a) adding the test sample to an in vitro culture of epithelial or endothelial cells; (b) adding an occludin loop peptide and the test sample to a second culture of the same cells; (c) incubating the cultures for such time under such conditions sufficient to observe growth in cultures containing no test sample; (d) comparing the extent of adhesion in cultures with test sample and peptide with the extent of adhesion in cultures with no peptide; and (e) determining the presence of inhibition by observation of more adhesion in cultures with test sample and less adhesion in cultures having test sample and peptide. In an alternate embodiment, the method for screening for the presence or absence of occludin inhibition by a test sample comprises: (a) adding the test sample to an in vitro culture of epithelial or endothelial cells; (b) adding an occludin loop peptide and the test sample to a second culture of the same cells; (c) adding a tracer compound to both cultures; (d) incubating the cultures for such time under such conditions sufficient to observe growth in cultures containing no test sample; (e) comparing the extent of tracer uptake in cultures with test sample and peptide with the extent of tracer uptake in cultures with no peptide; and (f) determining the presence of inhibition by observation of increased tracer uptake in cultures with test sample and decreased tracer uptake in cultures having test sample and peptide.

Compounds exhibiting activity are then tested for their ability to inhibit the barrier in cultured monolayers of epithelial cells. Compounds exhibiting activity in vitro in such assays are then tested in vivo and modified to eliminate toxic effects and optimize solubility or other properties required for certain applications. The invention provides a way to define compounds which can be co-administered with therapeutic drugs to enhance absorption to test on animals and humans. The unique sequence information is thus useful for the development therapeutically relevant compounds.

For example, in in vitro sealing experiments, peptides representing fragments of the sequence are first generation inhibitors. Testing those that inhibit may be further modified to provide second generation inhibitors, or be used to design mimicking compounds. Information from first generation inhibitors can also assist in screening libraries of compounds. Methods of the invention are applicable to any type of human tissue, including, but not limited to, oral and nasal mucosa, gut, dermal, blood vessel, and airway tissue.

In the practice of this aspect of the invention, drug delivery is enhanced in human patients by administration of an effective amount of an occludin inhibitor to the patient. By "occludin inhibitor" is meant any inhibitor of occludin function, occludin peptide fragments and analogues that bind to occludin receptors, antibodies to occludin or occludin fragments, occludin receptor antagonists, soluble receptor components that bind to occludin, antibodies to components of occludin receptors, and the like. Mixtures of inhibitors can also be employed, as well as inhibitors of occludin synthesis or stability. In some embodiments of the invention, inhibitors are administered with at least one other compound that enhances the inhibitory effect and/or stabilizes the inhibitor in the formulation administered.

Administration of occludin inhibitors can be local or systemic. Local administration is preferred in some embodiments. In these embodiments, at least one occludin inhibitor, preferably in association with a pharmaceutically acceptable carrier in which the inhibitor is dispersed or solubilized, is topically applied in effective amounts to the skin as a solution, lotion, cream, soap, and the like, or nasal mucosal and/or lung tissue using aerosols, inhalants, nasal drops, nasal sprays, and the like.

Systemic administration of occludin inhibitors in other embodiments can be via any method known in the art such as, for example, oral administration of losenges, tablets, capsules, granules, or other edible compositions; intravenous, intramuscular, or intradermal administration, e.g., by sterile injections; parenteral administration of fluids and the like. Combinations of therapies may also be employed.

The amount of occludin inhibitor necessary to bring about the therapeutic treatment is not fixed per se, and necessarily is dependent upon the drug delivery to be enhanced, the particular inhibitor employed, the particular drug employed in combination with occludin inhibitor, adjunct compounds in the composition administered that enhance the inhibitory effect where present, the age, weight, and clinical condition of the patient to be treated, and the concentrations of these ingredients in the formulation put together in association with a pharmaceutically acceptable carrier. Generally the dose should be sufficient to enhance drug delivery without producing unacceptable toxicity to the patient.

As mentioned above, compositions of the invention are typically applied in admixture with a pharmaceutically acceptable carrier or vehicle. Administration is facilitated and, in some cases, additional therapeutic effects are provided by the carrier. When a carrier is employed, it is necessary that the carrier be inert in the sense of not bringing about a deactivation of inhibitor, and in the sense of not bringing about any adverse effect to the patient to whom it is administered.

Suitable carriers include any that will dissolve or disperse the active ingredients at concentrations of active ingredients most suitable for use in the therapeutic treatment. Generally, even low concentrations of active ingredients in a carrier will be suitable, particularly where more frequent drug administration is required for enhancing drug therapy. It is desirable that compositions of the invention be formulated to contain amounts of inhibitor sufficient to provide enhancement of at least about 10%, preferably about 25% or higher, e.g., 50%, over the drug delivery in the absence of occludin inhibitor, or allow absorption of drugs that would otherwise not be absorbed. Accordingly, carriers will be chosen which can solubilize or disperse the active ingredients at such concentrations. Examples of such carriers include both aqueous and nonaqueous carriers. In addition, pharmaceutical compositions or formulations may also include other carriers, adjuvants, stabilizers, preservatives, dispersing agents, and the like.

It should be understood that in addition to the ingredients particularly mentioned above, formulations of the invention may include other agents conventional in the art having regard to the type of formulation in question, for example, those suitable for nasal administration may include odors, for oral administration, flavoring agents, and for topical applications, emollients.

Alternatively, isolated and purified human occludin supplies a polypeptide that can be used to provide methods of enhancing sealing for therapeutic purposes, such as, for example, by administration of effective amounts of occludin enhancers or modifiers of the allosteric seal effectors. It is an advantage of the invention that the elucidation of the structure of human occludin provides not only a way of enhancing transmucosal and transendothelial drug delivery, but also a way of reducing permeability.

While not wishing to be bound to any theory, the efficacy of the invention appears to be related to the selectivity in targeting occludin for the alteration of the intercellular seal. No presently used method for enhancing transmucosal or transvascular drug delivery takes advantage of knowledge of the tight junction's protein composition. Most approaches propose to alter intracellular signaling mechanisms and are likely to be quite nonselective in their action. In contrast, this invention uses the highly unusual chemistry of the extracellular domains of the sealing protein itself. It is an additional advantage of the invention that the target regions of occludin are extracellular so that antagonists which remain outside of cells can be developed which avoid interfering with intracellular events. This creates the possibility for an exquisitely specific effects of anti-occludin drugs.

EXAMPLES

The following examples are presented to further illustrate and explain the present invention and should not be taken as limiting in any regard.

Example 1

To clone the human occludin cDNA sequence, a short sequence homologous to the chicken cDNA sequence was observed fused to an unrelated cDNA presumed to encode the product of the NAIP gene in individuals afflicted with the genetic disease Spinal Muscular Atrophy (Roy, N., et al., *Cell* 80: 167–178 (1995)). It was assumed this represented a fragment of human occludin, and this sequence information was used to clone the full-length human occludin cDNA using standard techniques. Human RNA was reverse transcribed and amplified with oligonucleotide primers within the region homologous to chicken occludin. The expected amplification product was cloned and used to screen a human liver cDNA library, in a phagemid vector, using standard hybridization methods.

Multiple overlapping cDNAs were isolated, sequenced, and encoded the full-length occludin cDNA presented in FIG. 1. The deduced amino acid sequence show about 49% identity and about 66% similarity to chicken occludin. The two extracellular loop domains, residues 58–104 (residues 90 to 138 of SEQ ID NO: 2, inclusive) and 164–211 (residues 196 to 246 of SEQ ID NO: 2, inclusive), respectively, in human occludin, and residues 81–124 and 184–227 (inclusive) in chicken occludin show the same highly unusual chemistry.

Example 2

This example shows that occludin confers adhesiveness when expressed in fibroblasts.

cDNAs, Antibodies, Peptides and Cell Lines Employed

The 675-nucleotide occludin sequence found in the untranslated region of the human neuronal apoptosis inhibitory gene (Roy, N., et al., *Cell* 80: 167–178 (1995)) was used to design PCR primers, and reverse transcription-PCR was performed using polyA+ mRNA from Caco-2 cells as template. The resulting cDNA fragment was used to screen a human liver library (Clontech) and a full length cDNA was isolated and sequenced (GenBank Accession U53823). A similar protocol was recently reported by Ando-Akatsuka, et al., cited above, to clone the full-length human occludin, which demonstrates an exact match at the amino acid level to our sequence. The full length sequence was subcloned into the pCB6 expression vector with and without a 15 amino acid tag at the C-terminus. This tag represents the carboxy-terminus of the vesicular stomatitis virus glycoprotein (VSV-G).

A cDNA encoding the last 150 amino acids of human occludin was subcloned into the pGEX-1N vector and the resulting glutathione-S-transferase (GST) fusion protein used to generate anti-human occludin antibodies in guinea pigs. The same GST-fusion protein was also used to generate rabbit polyclonal antibodies using an accelerated immunization program referred to as PolyQuik™. The resultant rabbit polyclonal rabbit anti-human occludin polyclonal anti-sera was affinity purified using a GST-occludin coupled gel. Rabbit polyclonal anti-peptide antibodies raised against amino acids 90–112 of human occludin and two contiguous peptides: peptide #1 (CDRGYGTSLLGGSVGYPYGGSGFG, SEQ ID NO 3) and peptide #2 (CSYGSGYGYGYGYGYGYGGYTDPR, SEQ ID NO 4) were employed. Together these contiguous peptides compose the putative first extracellular loop of the occludin protein. Amino terminal cysteine residues are not part of the occludin sequence but were added to allow conjugation for antibody production. Because of the highly repetitive nature of the amino acid sequence of loop #1, it was difficult to design a control peptide by "scrambling" the sequence. Instead, a peptide from the putative cytoplasmic N-terminal region of occludin (NHYAPSNDIYGGEMVHRPML, SEQ ID NO 5), with the same isoelectric point (pI=6.2) as peptide #1, was used. Anti-ZO-1 antibody, secondary antibodies (FITC and Texas Red labelled) for immunofluorescence are affinity-purified, species-specific from Jackson Immunoresearch Laboratories (Westover, Iowa.) and for immunoblots from Amersham Corp. (Arlington Heights, Ill.) and Chemicon International, Inc. (Temecula, Calif.). Anti-VSV-G antibody was from MBL (Nagoya, Japan).

Tissue Culture and Cell Transfection

All cell lines were maintained in Dulbecco's modified Eagle's medium supplemented with 10% fetal bovine serum (Atlanta Biologicals, Norcross, Ga.) and antibiotics in 5% $CO_2$. Cells were transfected by calcium phosphate coprecipitation (Chen, C. A., and Okayama, A., *Biotechniques* 6: 632–638 (1988)); transient transfectants were induced with 5 mM sodium butyrate for 16–20 hours before immunofluorescent analysis. Occludin localization experiments were originally attempted after transient transfections, but results were variable and only results from stable cell lines are reported in this example. Stable cell lines were selected with 600 µg/ml G418 (Gibco BRL) for 10 days, at which time resistant clones were analyzed for occludin expression by immunofluorescence. Occludin-positive cells were maintained in 250 µg/ml G418.

Immunoblotting and Immunofluorescence

For immunoblot analysis, confluent Caco-2 cells were rinsed in phosphate-buffered saline (PBS) and lysed in sodium dodecyl sulfate (SDS) sample buffer and heated to 95° C. for 10 minutes. Control and stable occludin-expressing cell lines were plated at subconfluent density, allowed to attach and spread for 8 hours, and induced with 5 mM sodium butyrate for 16–20 hours. Cells were rinsed with PBS and samples prepared as above. Protein samples were separated by SDS 10% PAGE (Laemmli, U. K., *Nature* 227: 680–685 (1970)) and transferred to nitrocellulose (Towbin, H., et al., *Proc. Nat. Acad. Sci. USA* 76: 4350–4354 (1979)). Nonspecific protein binding was blocked with 10% nonfat dry milk, 0.1% Tween-20 in PBS for at least 1 hour at room temperature. Anti-occludin antibody (rabbit anti-human) was used at 1:1000 dilution, others as indicated in figure legends. Detection was by enhanced chemiluminescence (ECL, Amersham).

For immunofluorescent localization studies, cells were grown on glass coverslips. To demonstrate that the human occludin construct could be expressed and targeted appropriately in tight junction-containing cells, MDCK cells were used for the initial transient transfection assays. MDCK cells were transfected and induced with sodium butyrate as described above and stable cells lines were plated and induced as described for immunoblots. Cells were washed with PBS, fixed in 1% paraformaldehyde in PBS, extracted with 0.1% Triton-X 100 and quenched with 50 mM $NH_4Cl$ in PBS. In experiments to test the accessibility to the anti-peptide #1 antibody, incubation of the primary antibody was performed without permeabilization of cells with Triton-X 100. Cells were blocked for 1 hour in PBS plus 2% goat serum, incubated in primary antibodies (anti-VSV-G at 10 ug/ml, guinea pig anti-occludin at 1:250, and anti-ZO-1 at 1:300; affinity-purified anti-peptide #1 antibody at 1:10) for 1 hour, washed and incubated in affinity-purified secondary antibodies (1:100) for 1 hour. Cells were washed, dipped in $H_2O$ and mounted in Vectashield (Vector Laboratories). The samples were examined with a Nikon Microfot-FX epifluorescence microscope; photographs were taken with TMAX400 film (Kodak, Rochester, N.Y.) using the automatic exposure setting.

Cell Adhesion Assay

Adhesion of stably transfected cell lines was measured by a modification of the procedure described by Wesseling, J., et al., *Mol. Biol. Cell* 7:565–577 (1996). Cell lines were plated and induced with sodium butyrate as described above. Cell layers were rinsed twice with $Ca^{2+}$-$Mg^{2+}$-free PBS and then incubated for 30 minutes in $Ca^{2+}$-$Mg^{2+}$-free PBS plus 1 mM EDTA and 0.1 mg/ml DNAse. After 30 minutes, cells were mechanically dissociated, counted and resuspended at a concentration of $2.5 \times 10^5$ cells/ml in $Ca^{2+}$-$Mg^{2+}$-free PBS, 1 mM EDTA and 0.1 mg/ml DNAse. For each condition, the adhesion assay was performed in duplicate in two 50-ml conical tubes on a rotating platform at 80 rpm at 25° C. At each time point, the number of particles in two 175 ul aliquot of each tube was determined in a Coulter Counter (Hialeah, Fla.). The amount of adhesion was represented by $N_t/N_0$, where $N_0$ was the initial number of particles in each sample (the starting number of single cells), and $N_t$ was the number at each time point. 100% of cells were single at the beginning of all assays, as determined by phase-contrast microscopy. Some experiments were performed in the presence of the peptides described above.

Anti-human Occludin Antibodies

As described above, occludin cDNAs were isolated from a human liver library. The C-terminal 150 amino acids were subcloned into a pGEX vector and the resulting GST-fusion protein was used to generate polyclonal antibodies in guinea pigs. Use of these antibodies in Western blot analysis of the human colonic cell line, Caco-2, identified an antigen (doublet) at about 65 kDa, the same size as the antigen recognized previously (Fallon, M. B., et al., *Am. J. Physiol.* 260: C1057–1062 (1995)) by anti-chicken occludin antibody. Other antibodies used in these studies include a commercially available affinity-purified anti-human occludin rabbit polyclonal raised against the same C-terminal fusion protein and an anti-peptide antibody raised against a 23 amino acid sequence from the putative first extracellular loop (CDRGYGTSLLGGSVGYPYGGSGFG, SEQ ID NO 3). All antibodies recognize a doublet in Caco-2 cells. Multiple bands have been reported before and may result from an uncharacterized posttranslational modification. In addition, anti-chicken occludin antibodies recognize a smaller molecular weight protein of about 20 kDa; the nature of this cross-reacting epitope is unknown. Thus, all antibodies used in the present studies exclusively recognize occludin; results with the anti-chicken antibodies are shown to compare with our previously characterized antibodies but were not used for experiments reported herein.

Expression of Transfected Human Occludin in MDCK Cells

To confirm that transtected human occludin could localize appropriately in cells which normally expressed occludin, MDCK cells were transiently transfected with VSV-G-tagged human occludin cloned in the pCB6 vector. Expression was induced with sodium butyrate and cells stained for ZO-1 and for VSV-G. ZO-1 immunofluorescence reveals the typical reticular pattern of tight junction staining. Immunofluorescence using the VSV-G antibody shows that in cells that expressed low levels of human occludin, the transfected protein was concentrated at sites of cell-cell contact, although higher expressing cells also expressed considerable occludin elsewhere in the cell. It was concluded that the VSV-G-tagged human occludin can target appropriately to tight junctions in cultured epithelial cells which have pre-existing tight junctions.

Expression of Transfected Human Occludin in Fibroblast Cell Lines

The expression and localization of occludin were examined in three fibroblast cell lines that do not form recognizable tight junctions or electrically resistive monolayers in culture. NRK cells, Rat-1 cells and L-cells do not normally express detectable occludin by Western blot analysis. This apparent lack of expression is not due to an inability of the anti-human occludin antibody to recognize rodent occludin, since a slightly smaller form of occludin is easily detected in immunoblots from whole rat kidney. Fibroblast cells lines were transfected with the pCB6 occludin vector and stable cell lines were selected on the basis of antibiotic resistance with G418. G418-resistant clonal cell lines were screened by immunofluorescence and of the small number of occludin-expressing cell lines, none had more than about 40% of the cells expressing detectable occludin. Occiudin was readily detectable by Western blot analysis in some stable cell lines, and was inducible in all cell lines after 18 hours exposure to 5 mM sodium butyrate. The transfected human occludin exhibited a higher apparent molecular weight characteristic of human occludin when compared with rat occludin. The three fibroblast cell clones used for most of the following experiments could be induced to express approximately equal amounts of the occludin transgene. The inducible nature of occludin expression allowed comparison of uninduced with induced cell lines, as well as comparison to non-transfected cells. In addition, a Rat-1 cell clone (R11occ) expressing about one-third less occludin was used in some studies to look at the effect of expressing a lower level of occludin.

Yonemura, S., et al., *J. Cell Sci.* 108: 127–142 (1995) previously described that in NRK cells, ZO-1 localizes to sites of cell-cell contact, along with other proteins normally associated with adherens junctions. This ZO-1 distribution was also noted in NRK cells, as well as in another fibroblast line, Rat-1 cells, although the latter cells are not as flat and tend to have less regularly spaced cell contacts. In both NRK cells and in rat-i cells, human occludin colocalized with ZO-1 at sites of cell-cell contact, as well as showing a diffuse and lower level of expression over the entire plasma membrane. Occludin did not appear to be more concentrated between two neighboring cells when both expressed occludin, suggesting that in these transfected cells, intercellular occludin-occludin interactions do not appear to appreciably stabilize occludin localization. In fact, occludin appears to concentrate with ZO-1 even when the adjacent cell does not contain detectable occludin. Both transfected cell lines also had small amounts of occludin expressed elsewhere in the cell, possibly in intracellular vesicles and plasma membrane aggregates. In contrast, mouse L-cells, which lack E-cadherin and adherens-like junctions (Angres, B., et al., *J. Cell Biol.* 134(2):1–10 (1996)) concentrated neither ZO-1, nor occludin at sites of cell-cell contact. Both appear diffusely distributed over the plasma membrane, although ZO-1 but not occludin, is concentrated in puncta on the apical surface.

Occludin Expression Confers Adhesion on NRK and Rat-1 cells, but not L-cells

The ability of transfected occludin to confer adhesion onto fibroblast cell lines was assessed using a suspended cell aggregation assay (Wesseling, J., et al., *Mol. Biol. Cell* 7: 565–577 (1996)). All cells were counted as single particles at the beginning of the assay and any decrease in the fraction of particles over the 80 minute assay was the result of aggregates which are excluded by the Coulter Counter. Aggregation was qualitatively confirmed by light microscopic inspection and correlated with results quantified by the Coulter Counter. Immunofluorescence confirmed that ZO-1 and occludin are clustered between adherent cells after the 80 minute assay.

Figure 3A:
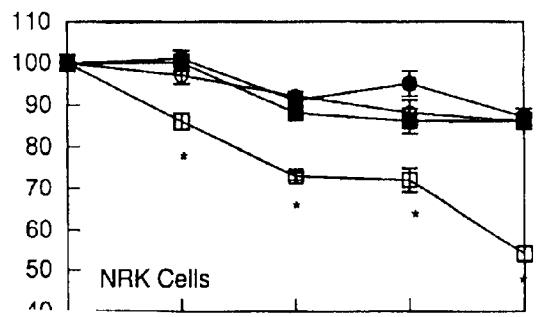
FIGS. 3A–3C show graphs comparing aggregation of human occludin-transfected cell lines. Occludin is expressed from a butyrate-inducible promoter. Aggregation kinetics of the various fibroblast cells lines (control untransfected NRK, rat-1 and L-cells) and occludin-transfected cell lines (N2occ, R9occ, L5occ) without (−) and with (+) 16 hours of butyrate induction as measured with the Coulter counter. The decrease in the relative percent of particles ($N_t/N_0 \times 100$) as a function of time indicates the extent of aggregation. The results from at least three separate experiments are combined; (*P<0.01, ANOVA).
Figure 3B:
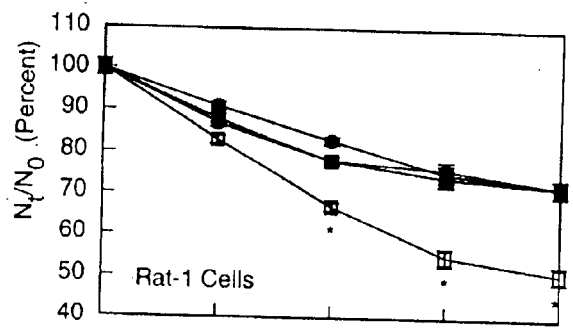
Figure 3C:
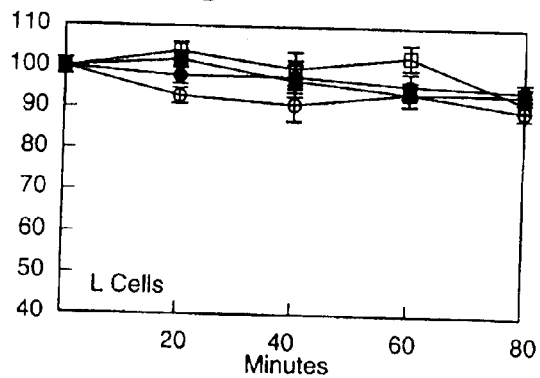
Figure 4:
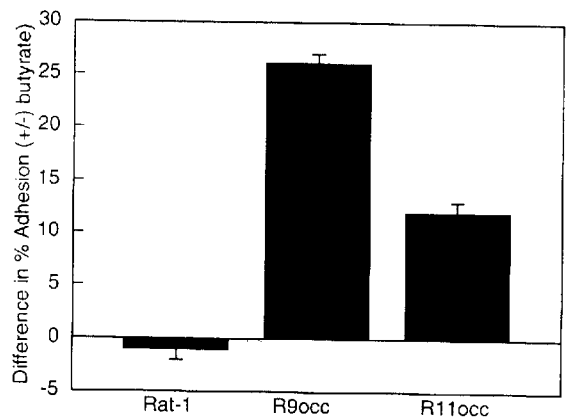
FIG. 4 compares aggregation in rat-1 cell clones. The difference in the percent of adhesion ($N_t/N_0 \times 100$) at 80 min in rat-1 cells without (−) and with (+) butyrate treatment is compared for the parent cell line (rat-1) and two occludin-transfected clones (R9occ and R11occ) which express different levels of human occludin. Results from three separate experiments are combined.

As shown in FIG. 3, human occludin promoted cell aggregation in the absence of calcium in both Rat-1 cells and in NRK fibroblasts, but not in L-cells. Expression of occludin in NRK and Rat-1 fibroblasts induced a steeper slope ($[N_t/N_0]$/time) and lower final number of particles per unit volume at 80 minutes, the longest time assayed. In addition, when two Rat-1 clones with differing levels of occludin expression were tested in this assay, the degree of adhesion at 80 minutes correlated in a positive way with the level of occludin expression (FIG. 4). It was not determined whether the degree of adhesion measured in this assay correlates with the level of occludin expresssed per cell or the percentage of cells expressing occludin. The effect of adhesion was not due to treatment of cells with butyrate, since adding butyrate to fibroblasts transfected with pCB6 without the occludin cDNA did not result in increased adhesion. The value of $[N_t/N_0 \times 100]$ never dropped below 40% suggesting some cells were nonadhesive. Although immunofluorescence studies showed not all cells express occludin, attempts to separate aggregated from single cells and determine whether nonaggregating cells were those showing less or no occludin expression were unsuccessful.

Antibody Accessibility Reveals Exposure of Occludin on the Extracellular Surface The model for occludin topography predicts a region rich in glycine and tyrosine is positioned as the first, or more N-terminal, of the two extracellular loops. To determine whether these sequences are exposed on the outside of the cell, their availability in nonperrneabilized living cells to an antibody raised against a synthetic peptide corresponding to the first 23 residues of this loop were assessed. As determined by Western blotting, these antibodies have very low affinity and consistent results were only obtained using human Caco-2 cells which contain many fold higher levels of occludin that did the transfected cells. The C-terminal ZO-1 binding domain of occludin was previously shown to be intracellular (Furuse, el al., cited above) and consistent with this, immunofluorescence analysis of nonpermeabilized Caco-2 cells stained with an antibody to this region reveals no specific staining. After detergent permeabilization, the same antibody reveals a typical reticular occludin staining pattern. Nonpermeabilized Caco-2 cells incubated in 1 mM EDTA and antibody raised against the putative extracellular sequence shows a similar pattern of staining, suggesting this sequence is in fact exposed on cell surface. Less labeling was observed when cells were not exposed to EDTA, suggesting the sequences are not available to bind antibodies unless contacts are first disrupted by chelating divalent cations. However, even after exposure to EDTA the antigen is not uniformly accessible. However, the antibody accessibility proves the putative extracellular loop is indeed extracellular, and a target for occludin inhibitors.

Occludin Peptides Inhibit Occludin-induced Adhesion

Figure 5A:
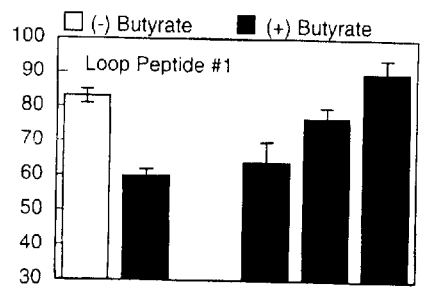
FIGS. 5A–5C shows aggregation of N2occ cells in the absence or presence of various concentrations of synthetic peptides. Peptides were added in equal volumes of PBS at the start of the incubation period; extent of aggregation is shown after 80 minutes of incubation. Loop peptides represent contiguous sequences in the first extracellular loop (SEQ ID NOs 3 and 4); the internal peptide has the same pI as loop peptide #1. Peptide sequences are given in the Examples section. One of three experiments with identical results is shown.
Figure 5B:
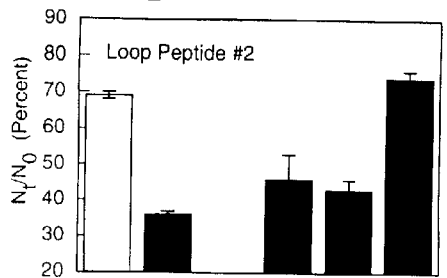
Figure 5C:
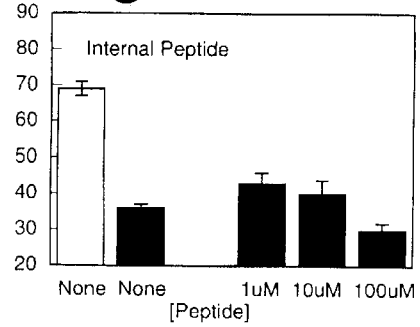

To determine if the extracellular sequences of occludin are directly involved in the adhesion observed in the occludin-transfected fibroblasts, an assessment of competition for the adhesive function using synthetic peptides corresponding to both halves of the first putative extracellular loop was attempted (FIG. 5). Peptides were tested at 1, 10 and 100 $\mu$M. Both peptides #1 and #2 completely inhibited adhesion in both the Rat-1 and NRK cell clones at 100 $\mu$M (Rat-1 cell). Peptide #1 reversed approximately half the adhesion at 10 $\mu$M, suggesting an apparent $K_i$ in this range. The apparent $K_i$ for peptide #2 was reproducibly somewhat higher, in the range between 10–100 $\mu$M. These apparent inhibition constants suggest this region of occludin participates in a relatively low affinity binding interaction. An internal occludin peptide added over the same concentration range was ineffective at inhibiting occludin-dependent cell adhesion.

Discussion and Conclusions

Thus, transfected human occludin colocalizes with ZO-1 at sites of cell-cell contact in some fibroblast cell lines, and cells in which occludin colocalizes acquire adhesiveness. In addition, it was shown shown that the putative first extracellular loop of occludin is accessible to antibodies in the absence of cell permeabilization, thus supporting the predicted transmembrane topology originally based on hydrophobicity profiles (Furuse, et at., cited above). Finally, it was demonstrated that peptides with sequences matching this extracellular loop decrease cell adhesion in occludin-expressing fibroblasts in a dose-dependent fashion. These data imply that this loop participates in an adhesive interaction, and the peptides are acting as competitive inhibitors at the adhesive surface.

The human occludin used herein was capable of properly targeting when expressed in cultured epithelial cells which contain preformed tight junctions (MDCK cells). In contrast, when expressed ectopically in fibroblasts, occludin localized only at cell-cell contacts in lines already capable of localizing ZO-1, i.e. NRK cells and Rat-1 cells. ZO-1 is known to bind directly to occludin through a 150 amino domain at the C-terminus of occludin (Furuse, et al., cited above). Without wishing to be bound to any theory, it appears from observations in fibroblasts is that occludin uses prelocalized ZO-1 as its predominate targeting signal. This observation is different than that of Balda, M. S., et al., *J. Cell Biol.* 134(4): 1031–1049 (1996), who expressed a truncated form of occludin without the ZO-1 binding domain in MDCK cells and found it still capable of targeting to the tight junction. Because these cells already contain preformed tight junctions, lateral interactions between occludin proteins within the same cell or between cells could account for localization. However, in the absence of endogenous occludin, de novo targeting of occludin in fibroblasts appears to require binding to ZO-1, not lateral or cell-cell association between occludin proteins.

Neither ZO-1 nor ectopically-expressed occludin was capable of localizing to cell contacts in the L-cell clone used for this study. Occludin was diffusely distributed over the cell, again suggesting that accumulation at cell contacts is not a strong intrinsic property of occludin. This L-cell clone was previously shown to express very low levels of cadherin, and consistent with this it lacks $Ca^{2+}$-dependent adhesion (Angres et al., 1996). It was recently shown that the cadherin-binding protein β-catenin binds to ZO-1 early after initiation of cell contacts, and that these proteins subsequently sort over time into distinct tight and adherens junctions (Rajasekaran, A. K., et al., *J. Cell Biol.* 132:451–463 (1996)). Interaction with cadherin through B-catenin provides a tentative explanation for why ZO-1 clusters at cadherin contacts in occludin-null cells and why ectopically-expressed occludin fails to cluster in cells which lack cadherin. The cell-cell contacts of NRK cells have been shown to contain several components of adherens-type junctions, vinculin, a-actinin (Yonemura, S., et al., *J. Cell Sci.* 108:127–142 (1995)), thus direct or indirect interaction with any of these could conceivably also provide a mechanism to recruit ZO-1 and occludin.

The results suggest a correlation in fibroblasts between the ability of occludin to cluster at cell—cell contacts and confer adhesiveness. Without wishing to be bound to any theory, one possible explanation is that occludin molecules must cluster to gain sufficient cooperativity for adhesiveness to be detected in the assay employed here. Other circumstantial evidence also suggests occludin's adhesiveness is not inherently high. For example, as judged by immunofluorescence, no more occludin accumulates between two fibroblasts which both express occludin than between null cells and expressing cells. In addition, even when expressed on two adjacent cells, occludin never promotes a continuous linear, tight junction-like, contact and its expression does not seem to morphologically alter the pre-existent ZO-1 containing contact. Another explanation for the correlation between clustering and adhesion might be that occludin must interact with cytoplasmic proteins present in the plaque to induce an adhesive conformation. Both models are consistent with the known properties of other adhesion molecules, such as the integrins, which increase adhesion through clustering as well as through conformational changes induced from the cytoplasmic side (Dehar, S., and Hannigan, G. E., *Current Opinion in Cell Biology* 8: 657–669 (1996)).

McCarthy, K. M., et al., *J. Cell Sci.* 109:2287–2298 (1996) demonstrated the colocalization of ZO-1 and chicken occludin in MDCK cells cultured in low calcium, both in vesicular structures within cells and occasionally between cell pairs, consistent with the idea that ZO-1-occludin interactions can be maintained in the absence of $Ca^{2+}$. It was demonstrated herein that occludin is adhesive in the absence of calcium, although one possiblility is that occludin merely enhances cadherin-based adhesion, or adhesion due to other cell suface proteins, even in low calcium. It seems more likely that the longstanding observation that tight junction formation is dependent on calcium-dependent cadherin-dependent cell contact may be based on the requirement of cadherin to induce the highly organized and adhesive state of occludin within the tight junction and not a requirement for cadherin as a co-adhesive receptor. Contrasting results in NRK and Rat-1 cells with L-cells suggests the testable hypothesis that clustering and or interaction with ZO-1, and not cadherin per se is required to observe adhesion.

Occludin has been proposed to have two extracellular loops, based on four predicted hydrophobic transmembrane helices and immunologic evidence that the C-terminus is intracellular (Furuse, et al., cited above). It was confirmed that at least the first of these loops is in fact extracellular, since it is accessible in a nonpermeabilized cell to an antibody generated to a peptide sequence contained within this loop. This example focuses on the first extracellular loop because it is the least conserved and thus may provide species-specific recognition. Recent work of Wong and Gumbiner, cited above, have demonstrated that a peptide consisting of the chicken sequence for the second loop blocked transepithelial electrical resistance when applied to cultured monolayers of Xenopus A6 cells. In their assay, a peptide consisting of the first loop of the chicken sequence had no effect on transepithelial electrical resistance, consistent with the possibility for a species specific sequence requirement.

It was shown that two separate peptides containing contiguous sequences of the first extracellular loop are both capable of inhibiting adhesion in the occludin-transfected fibroblasts. Similar methods have been used to inhibit the function of other cell adhesion molecules; for example, small peptides containing extracellular loop sequences for connexins delay gap junction formation (Warner, A., et al., *J. Physiol.* 488(3):721–728 (1995)), and a cadherin extracellular peptide inhibits embryo compaction (Blaschuk, O. W., et al., *Dev. Biol.* 139(1):227–229 (1990)) and contact-dependent granulosa cell apoptosis (Peluso, J. J., et al., *Endocrin.* 137(4):1196–1203 (1996)). While not wishing to be bound to any theory, it seems that the extracellular loops of occludin are involved in binding a protein on the adjacent cell, either through a homophilic interaction or with some other binding partner. Consistent with the possibility that occludin is a homophilic adhesion protein is its induction of adhesion in previously occludin-null fibroblasts.

The apparent $K_i$ in the fibroblast assay for both peptides is in the range of 10–100 $\mu$M, suggesting a relatively low affinity. The observation that both non-overlapping peptides, which together represent the entire first loop, separately inhibit adhesion suggests the protein interaction surface may include the entire loop. This would be consistent with the observation that among the five occludin sequences available, it is the unusual composition of the loop, and not necessarily its primary sequence, which is conserved (Ando-Akatsuka, cited above). Occludin has been show to be a component of the tight junction strands visualized in by freeze fracture electron microscopy (Fujimoto, K., *J. Cell Sci.*, 108:3443–3449 (1995)). The ability to form linear polymers in the plasma membrane and interact over an extensive protein surface may be the mechanism by which occludin creates a molecular-level barrier across the paracellular pathway.

The results confirm the topography of occludin, demonstrate occludin's ability to induce adhesion when expressed in cells lacking tight junctions and suggest it must be clustered or interact with cytoplasmic proteins in order to be adhesive. Together these results suggest testable models for how the occludin-based intercellular seal of the tight junction is created by both the specific chemistry of its extracellular loops and by influences of cytoplasmic plaque proteins.

The above description is for the purpose of teaching the person of ordinary skill in the art how to practice the present invention, and it is not intended to detail all those obvious modifications and variations of it which will become appar ent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The papers cited above are expressly incorporated herein in their entireties by reference.

What is claimed is:

1. An isolated and purified human occludin polypeptide shown in SEQ ID NO: 2.

2. A polypeptide corresponding to residues 90 to 138 of SEQ ID NO:2.

3. A polypeptide corresponding to residues 196 to 246 of SEQ ID NO: 2.

4. A method for screening for the presence or absence of occludin inhibition by a test sample comprising:
   (a) adding the test sample to an in vitro culture of epithelial or endothelial cells;
   (b) adding an occludin peptide according to claim 2 and the test sample to a second culture of the same cells;
   (c) incubating the cultures for such time under such conditions sufficient to observe growth in cultures containing no test sample;
   (d) comparing the extent of adhesion in cultures with test sample and peptide with the extent of adhesion in cultures with no peptide; and
   (e) determining the presence of inhibition by observation of more adhesion in cultures with test sample and less adhesion in cultures having test sample and peptide.

5. A method for screening for the presence or absence of occludin inhibition by a test sample comprising:
   (a) adding the test sample to an in vitro culture of epithelial or endothelial cells;
   (b) adding an occludin peptide according to claim 2 to a second culture of the same cells;
   (c) adding a tracer compound to both cultures;
   (d) incubating the cultures for such time under such conditions sufficient to observe growth in cultures containing no test sample;
   (e) comparing the extent of tracer uptake in cultures with test sample and peptide with the extent of tracer uptake in cultures with no peptide; and
   (f) determining the presence of inhibition by observation of increased tracer uptake in cultures with test sample and decreased tracer uptake in cultures having test sample and peptide.

6. A method for screening for the presence or absence of occludin inhibition by a test sample comprising:
   (a) adding the test sample to an in vitro culture of epithelial or endothelial cells;
   (b) adding an occludin peptide according to claim 3 and the test sample to a second culture of the same cells;
   (c) incubating the cultures for such time under such conditions sufficient to observe growth in cultures containing no test sample;
   (d) comparing the extent of adhesion in cultures with test sample and peptide with the extent of adhesion in cultures with no peptide; and
   (e) determining the presence of inhibitiion by observation of more adhesion in cultures with test sample and less adhesion in cultues having test sample and peptide.

7. A method for screening for the presence or absence of occludin inhibition by a test sample comprising:
   (a) adding the test sample to an in vitro culture of epithelial or endothelial cells;
   (b) adding an occludin peptide according to claim 3 to a second culture of the same cells;
   (c) adding a tracer compound to both cultures;
   (d) incubating the cultures for such time under such conditions sufficient to observe growth in cultures containing no test sample;
   (e) comparing the extent of tracer uptake in cultures with test sample and peptide with the extent of tracer uptake in cultures with no peptide; and (f) determining the presence of inhibition by observation of increased tracer uptake in cultures with test sample and decreased tracer uptake in cultures having test sample and peptide.

8. A method for screening for the presence or absence of occludin inhibition by a test sample comprising:
   (a) adding the test sample to an in vitro culture of epithelial or endothelial cells;
   (b) adding the occludin polypeptide according to claim 1 and the test sample to a second culture of the same cells;
   (c) incubating the cultures for such time under such conditions sufficient to observe growth in cultures containing no test sample;
   (d) comparing the extent of adhesion in cultures with test sample and peptide with the extent of adhesion in cultures with no polypeptidepeptide; and
   (e) determining the presence of inhibition by observation of more adhesion in cultures with test sample and less adhesion in cultures having test sample and polypeptide.

9. A method for screening for the presence or absence of occludin inhibition by a test sample comprising:
   (a) adding the lest sample to an in vitro culture of epithelial or endothelial cells;
   (b) adding the occludin polypeptide according to claim 1 to a second culture of the same cells;
   (c) adding a tracer compound to both cultures;
   (d) incubating the cultures for such time under such conditions sufficient to observe growth in cultures containing no test sample;
   (e) comparing the extent of tracer uptake in cultures with test sample and peptide with the extent of tracer uptake in cultures with no polypeptide; and
   (f) determining the presence of inhibition by observation of increased tracer uptake in cultures with test sample and decreased tracer uptake in culuires having test sample and polypeptide.

10. A method for screening for the presence or absence of occludin inhibition by a test sample comprising:
    (a) adding the test sample to a fibroblast culture;
    (b) adding the occludin polypeptide according to claim 1 and the test sample to a second culture of the same fibroblasts;
    (c) incubating. the cultures for such time under such conditions sufficient to observe adhesion;
    (d) comparing the extent of adhesion in cultures with test sample and peptide with the extent of adhesion in cultures with no polypeptide; and
    (e) determining the presence of inhibition by observation of more adhesion in cultures with test sample and less adhesion in cultures having test sample and polypeptide.

11. A method for screening for the presence or absence of occludin inhibition by a test sample comprising:
    (a) adding the test sample to a fibroblast culture;
    (b) adding the occludin peptide according to claim 2 and the test sample to a second culture of the same fibroblasts;
    (c) incubating the cultures for such time under such conditions sufficient to observe adhesion;
    (d) comparing the extent of adhesion in cultures with test sample and peptide with the extent of adhesion in cultures with no peptide; and
    (e) determining the presence of inhibition by observation of more adhesion in cultures with test sample and less adhesion in cultures having test sample and peptide.

12. A method for screening for the presence or absence of occludin inhibition by a test sample comprising:
    (a) adding the test sample to a fibroblast culture;
    (b) adding the occludin peptide according to claim 3 and the test sample a second culture of the same fibroblasts;
    (c) incubating the cultures for such time under such conditions sufficient to observe adhesion;
    (d) comparing the extent of adhesion in cultures with test sample and peptide with the extent of adhesion in cultures with no peptide; and
    (e) determining the presence of inhibition by observation of more adhesion in cultures with test sample and less adhesion in cultures having test sample and peptide.

13. A method according to claim 4 wherein adhesion is measured using electrical resistance measurements or trans-monolayer flux measurements.

14. A method according to claim 6 wherein adhesion is measured using electrical resistance measurements or trans-monolayer flux measurements.

15. A method according to claim 8 wherein adhesion is measured using electrical resistance measurements or trans-monolayer flux measurements.

16. A method according to claim 10 wherein adhesion is measured using electrical resistance measurements or trans-monolayer flux measurements.

17. A method according to claim 11 wherein adhesion is measured using electrical resistance measurements or trans-monolayer flux measurements.

18. A method according to claim 12 wherein adhesion is measured using electrical resistance measurements or trans-monolayer flux measurements.

* * * * *

UNITED STATES PATENT AND TRADEMARK OFFICE
CERTIFICATE OF CORRECTION

PATENT NO. : 6,252,045 B1
DATED : June 26, 2001
INVENTOR(S) : James M. Anderson and Christina M. Van Itallie It is certified that error appears in the above-identified patent and that said Letters Patent is hereby corrected as shown below:

<u>Title page,</u>
Add the following references to the References Cited publications list:
-- Anderson, J.M., & Van Itallie, C.M., *Am. J. Physiol. (GI and Liver) 269*: G467-G475 (1995).
Ando-Akatsuka, Y., *et al.*, *J. Cell Biology 133*: 43-47 (1996).
Furuse, M., *et al.*, *J. Cell Biology 123*: 1777-1778 (1993).
Hirase, T., *et al.*, *J. Cell Sci. 110*: 1603 (1997) [abstract]
Kevil, C.G., et al., *Microcirculation 5*: 197 (1998) [abstract].
McCarthy, K.A., *et al.*, *J. Cell Sci. 109*: 2287-2298 (1996).
Mitic, L.L., & Anderson, J.M., *Annu. Rev. Physiol. 60*: 121-142 (1998).
Van Itallie, C.M., & Anderson, J.M., *J. Cell Sci. 110*: 1113-1121 (1997).
Wong, V., & Gumbiner, B.M., *J. Cell Biology 136*: 399-409 (1997).

Signed and Sealed this

Second Day of April, 2002

Attest:

JAMES E. ROGAN
*Attesting Officer*       *Director of the United States Patent and Trademark Office*

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 2312
      (B) TYPE: nucleic acid
      (C) STRANDEDNESS: single
      (D) TOPOLOGY: linear (ii) MOLECULE TYPE:
      (A) DESCRIPTION: cDNA (v) FRAGMENT TYPE: complete sequence (ix) FEATURE:
      (A) NAME/KEY: human occludin (xi) SEQUENCE DESCRIPTION: SEQ ID NO: 1:

```
GCCTCTCTCC ATCAGACACC CCAAGGTTCC ATCCGAAGCA GGCGGAGCAC          50

CGAACGCACC CCGGGGTGGT CAGGGACCCC CATCCGTGCT GCCCCCTAGG         100

AGCCCGCGCC TCTCCTCTGC GCCCCGCCTC TCGGGCCGCA ACATCGCGCG         150

GTTCCTTTAA CAGCGCGCTG GCAGGGTGTG GGAAGCAGGA CCGCGTCCTC         200

CCGCCCCCTC CCATCCGAGT TTCAGGTGAA TTGGTCACCG AGGGAGGAGG         250

CCGACACACC ACACCTACAC TCCCGCGTCC ACCTCTCCCT CCCTGCTTCC         300

TCTTGGCGGA GGCGGCAGGA ACCGAGAGCC AGGTCCAGAG CGCCGAGGAG         350

CCGGTCTAGG ACGCAGCAGA TTGGTTTATC TTGGAAGCTA AAGGGCATTG         400

CTCATCCTGA AGATCAGCTG ACCATTGACA ATCAGCCATG TCATCCAGGC         450

CTCTTGAAAG TCCACCTCCT TACAGGCCTG ATGAATTCAA ACCGAATCAT         500

TATGCACCAA GCAATGACAT ATATGGTGGA GAGATGCATG TTCGACCAAT         550

GCTCTCTCAG CCAGCCTACT CTTTTTACCC AGAAGATGAA ATTCTTCACT         600

TCTACAAATG GACCTCTCCT CCAGGAGTGA TTCGGATCCT GTCTATGCTC         650

ATTATTGTGA TGTGCATTGC CATCTTTGCC TGTGTGGCCT CCACGCTTGC         700

CTGGGACAGA GGCTATGGAA CTTCCCTTTT AGGAGGTAGT GTAGGCTACC         750

CTTATGGAGG AAGTGGCTTT GGTAGCTACG GAAGTGGCTA TGGCTATGGC         800

TATGGTTATG GCTATGGCTA CGGAGGCTAT ACAGACCCAA GAGCAGCAAA         850

GGGCTTCATG TTGGCCATGG CTGCCTTTTG TTTCATTGCC GCGTTGGTGA         900

TCTTTGTTAC CAGTGTTATA AGATCTGAAA TGTCCAGAAC AAGAAGATAC         950

TACTTAAGTG TGATAATAGT GAGTGCTATC CTGGGCATCA TGGTGTTTAT        1000

TGCCACAATT GTCTATATAA TGGGAGTGAA CCCAACTGCT CAGTCTTCTG        1050

GATCTCTATA TGGTTCACAA ATATATGCCC TCTGCAACCA ATTTTATACA        1100

CCTGCAGCTA CTGGACTCTA CGTGGATCAG TATTTGTATC ACTACTGTGT        1150
```

-continued

| Sequence | Position |
|---|---|
| TGTGGATCCC CAGGAGGCCA TTGCCATTGT ACTGGGGTTC ATGATTATTG | 1200 |
| TGGCTTTTGC TTTAATAATT TTCTTTGCTG TGAAAACTCG AAGAAAGATG | 1250 |
| GACAGGTATG ACAAGTCCAA TATTTTGTGG ACAAGGAAC ACATTTATGA | 1300 |
| TGAGCAGCCC CCCAATGTCG AGGAGTGGGT TAAAAATGTG TCTGCAGGCA | 1350 |
| CACAGGACGT GCCTTCACCC CCATCTGACT ATGTGGAAAG AGTTGACAGT | 1400 |
| CCCATGGCAT ACTCTTCCAA TGGCAAAGTG AATGACAAGC GGTTTTATCC | 1450 |
| AGAGTCTTCC TATAAATCCA CGCCGGTTCC TGAAGTGGTT CAGGAGCTTC | 1500 |
| CATTAACTTC GCCTGTGGAT GACTTCAGGC AGCCTCGTTA CAGCAGCGGT | 1550 |
| GGTAACTTTG AGACACCTTC AAAAAGAGCA CCTGCAAAGG GAAGAGCAGG | 1600 |
| AAGGTCAAAG AGAACAGAGC AAGATCACTA TGAGACAGAC TACACAACTG | 1650 |
| GCGGCGAGTC CTGTGATGAG CTGGAGGAGG ACTGGATCAG GGAATATCCA | 1700 |
| CCTATCACTT CAGATCAACA AGACAACTG TACAAGAGGA ATTTTGACAC | 1750 |
| TGGCCTACAG GAATACAAGA GCTTACAATC AGAACTTGAT GAGATCAATA | 1800 |
| AAGAACTCTC CCGTTTGGAT AAAGAATTGG ATGACTATAG AGAAGAAAGT | 1850 |
| GAAGAGTACA TGGCTGCTGC TGATGAATAC AATAGACTGA AGCAAGTGAA | 1900 |
| GGGATCTGCA GATTACAAAA GTAAGAAGAA TCATTGCAAG CAGTTAAAGA | 1950 |
| GCAAATTGTC ACACATCAAG AAGATGGTTG GAGACTATGA TAGACAGAAA | 2000 |
| ACATAGAAGG CTGATGCCAA GTTGTTTGAG AAATTAAGTA TCTGACATCT | 2050 |
| CTGCAATCTT CTCAGAAGGC AAATGACTTT GGACCATAAC CCCGGAAGCC | 2100 |
| AAACCTCTGT GAGCATCACA AAGTTTTGGG TTGCTTTAAC ATCATCAGTA | 2150 |
| TTGAAGCATT TTATAAATCG CTTTTGATAA TCAACTGGGC TGAACAACTC | 2200 |
| CAATTAAGGA TTTTATGCTT TAAACATTGG TTCTTGTATT AAGAATGAAA | 2250 |
| TACTGTTTGA GGTTTTTAAG CCTTAAAGGA AGGTTCTGGT GTGAACTAAA | 2300 |
| CTTTCACACC CC | 2312 |

(2) INFORMATION FOR SEQ ID NO: 2:

(i) SEQUENCE CHARACTERISTICS:
        (A) LENGTH: 522
        (B) TYPE: amino acid
        (C) STRANDEDNESS: single
        (D) TOPOLOGY: linear (ii) MOLECULE TYPE:
        (A) DESCRIPTION: polypeptide (v) FRAGMENT TYPE: complete sequence (ix) FEATURE:
        (A) NAME/KEY: human occludin (xi) SEQUENCE DESCRIPTION: SEQ ID NO: 2:

Met Ser Ser Arg Pro Leu Glu Ser Pro Pro Tyr Arg Pro Asp
            5                    10                  15

Glu Phe Lys Pro Asn His Tyr Ala Pro Ser Asn Asp Ile Tyr Gly
            20                    25                  30

Gly Glu Met His Val Arg Pro Met Leu Ser Gln Pro Ala Tyr Ser
            35                    40                  45

Phe Tyr Pro Glu Asp Glu Ile Leu His Phe Tyr Lys Trp Thr Ser
            50                    55                  60

```
Pro Pro Gly Val Ile Arg Ile Leu Ser Met Leu Ile Ile Val Met
                65                   70                  75

Cys Ile Ala Ile Phe Ala Cys Val Ala Ser Thr Leu Ala Trp Asp
                80                   85                  90

Arg Gly Tyr Gly Thr Ser Leu Leu Gly Gly Ser Val Gly Tyr Pro
                95                  100                 105

Tyr Gly Gly Ser Gly Phe Gly Ser Tyr Gly Ser Gly Tyr Gly Tyr
               110                  115                 120

Gly Tyr Gly Tyr Gly Tyr Gly Tyr Gly Gly Tyr Thr Asp Pro Arg
               125                  130                 135

Ala Ala Lys Gly Phe Met Leu Ala Met Ala Ala Phe Cys Phe Ile
               140                  145                 150

Ala Ala Leu Val Ile Phe Val Thr Ser Val Ile Arg Ser Glu Met
               155                  160                 165

Ser Arg Thr Arg Arg Tyr Tyr Leu Ser Val Ile Val Ser Ala
               170                  175                 180

Ile Leu Gly Ile Met Val Phe Ile Ala Thr Ile Val Tyr Ile Met
               185                  190                 195

Gly Val Asn Pro Thr Ala Gln Ser Ser Gly Ser Leu Tyr Gly Ser
               200                  205                 210

Gln Ile Tyr Ala Leu Cys Asn Gln Phe Tyr Thr Pro Ala Ala Thr
               215                  220                 225

Gly Leu Tyr Val Asp Gln Tyr Leu Tyr His Tyr Cys Val Val Asp
               230                  235                 240

Pro Gln Glu Ala Ile Ala Ile Val Leu Gly Phe Met Ile Ile Val
               245                  250                 255

Ala Phe Ala Leu Ile Ile Phe Phe Ala Val Lys Thr Arg Arg Lys
               260                  265                 270

Met Asp Arg Tyr Asp Lys Ser Asn Ile Leu Trp Asp Lys Glu His
               275                  280                 285

Ile Tyr Asp Glu Gln Pro Pro Asn Val Glu Glu Trp Val Lys Asn
               290                  295                 300

Val Ser Ala Gly Thr Gln Asp Val Pro Ser Pro Ser Asp Tyr
               305                  310                 315

Val Glu Arg Val Asp Ser Pro Met Ala Tyr Ser Ser Asn Gly Lys
               320                  325                 330

Val Asn Asp Lys Arg Phe Tyr Pro Glu Ser Ser Tyr Lys Ser Thr
               335                  340                 345

Pro Val Pro Glu Val Val Gln Glu Leu Pro Leu Thr Ser Pro Val
               350                  355                 360

Asp Asp Phe Arg Gln Pro Arg Tyr Ser Ser Gly Gly Asn Phe Glu
               365                  370                 375

Thr Pro Ser Lys Arg Ala Pro Ala Lys Gly Arg Ala Gly Arg Ser
               380                  385                 390

Lys Arg Thr Glu Gln Asp His Tyr Glu Thr Asp Tyr Thr Thr Gly
               395                  400                 405

Gly Glu Ser Cys Asp Glu Leu Glu Asp Trp Ile Arg Glu Tyr
               410                  415                 420

Pro Pro Ile Thr Ser Asp Gln Gln Arg Gln Leu Tyr Lys Arg Asn
               425                  430                 435

Phe Asp Thr Gly Leu Gln Glu Tyr Lys Ser Leu Gln Ser Glu Leu
               440                  445                 450

Asp Glu Ile Asn Lys Glu Leu Ser Arg Leu Asp Lys Glu Leu Asp
```

```
                    455                 460                 465
Asp Tyr Arg Glu Glu Ser Glu Glu Tyr Met Ala Ala Asp Glu
                470                 475                 480
Tyr Asn Arg Leu Lys Gln Val Lys Gly Ser Ala Asp Tyr Lys Ser
                485                 490                 495
Lys Lys Asn His Cys Lys Gln Leu Lys Ser Lys Leu Ser His Ile
                500                 505                 510
Lys Lys Met Val Gly Asp Tyr Asp Arg Gln Lys Thr
                515                 520
```

(2) INFORMATION FOR SEQ ID NO: 3:

(i) SEQUENCE CHARACTERISTICS:
        (A) LENGTH: 24
        (B) TYPE: amino acid
        (C) STRANDEDNESS: single
        (D) TOPOLOGY: linear (ii) MOLECULE TYPE:
        (A) DESCRIPTION: peptide (v) FRAGMENT TYPE: synthetic peptide (ix) FEATURE:
        (D) OTHER INFORMATION: construct used in experiments (xi) SEQUENCE DESCRIPTION: SEQ ID NO: 3:

```
Cys Asp Arg Gly Tyr Gly Thr Ser Leu Leu Gly Gly Ser Val Gly
                5                   10                  15
Tyr Pro Tyr Gly Gly Ser Gly Phe Gly
                20
```

(2) INFORMATION FOR SEQ ID NO: 4:

(i) SEQUENCE CHARACTERISTICS:
        (A) LENGTH: 24
        (B) TYPE: amino acid
        (C) STRANDEDNESS: single
        (D) TOPOLOGY: linear (ii) MOLECULE TYPE:
        (A) DESCRIPTION: peptide (v) FRAGMENT TYPE: synthetic peptide (ix) FEATURE:
        (D) OTHER INFORMATION: construct used in experiments (xi) SEQUENCE DESCRIPTION: SEQ ID NO: 4:

```
Cys Ser Tyr Gly Ser Gly Tyr Gly Tyr Gly Tyr Gly Tyr
                5                   10                  15
Gly Tyr Gly Gly Tyr Thr Asp Pro Arg
                20
```

(2) INFORMATION FOR SEQ ID NO: 5:

(i) SEQUENCE CHARACTERISTICS:
        (A) LENGTH: 20
        (B) TYPE: amino acid
        (C) STRANDEDNESS: single
        (D) TOPOLOGY: linear (ii) MOLECULE TYPE:
        (A) DESCRIPTION: peptide (v) FRAGMENT TYPE: synthetic peptide

```
        (ix) FEATURE:
              (D) OTHER INFORMATION: construct used in experi-
                  ments (xi) SEQUENCE DESCRIPTION: SEQ ID NO: 5:

Asn His Tyr Ala Pro Ser Asn Asp Ile Tyr Gly Gly Glu Met Val
                  5                  10                  15

His Arg Pro Met Leu
              20

(2) INFORMATION FOR SEQ ID NO: 6:

(i) SEQUENCE CHARACTERISTICS:
              (A) LENGTH:  11
              (B) TYPE: amino acid
              (C) STRANDEDNESS: single
              (D) TOPOLOGY: linear (ii) MOLECULE TYPE:
              (A) DESCRIPTION: peptide (v) FRAGMENT TYPE: synthetic peptide (ix) FEATURE:
              (D) OTHER INFORMATION: construct used in experi-
                  ments (xi) SEQUENCE DESCRIPTION: SEQ ID NO: 6:

Ala Ser Gln Gln Val Tyr Arg Lys Asp Pro Cys
                  5                  10
```